United States Patent [19]

Riemenschneider et al.

[11] 3,989,753

[45] Nov. 2, 1976

[54] PROCESS FOR THE PREPARATION OF OXAMIDE

[75] Inventors: Wilhelm Riemenschneider, Frankfurt am Main; Peter Wegener, Schneidhain, Taunus, both of Germany

[73] Assignee: Hoecht Aktiengesellschaft, Frankfurt (Main) Germany

[22] Filed: Feb. 21, 1974

[21] Appl. No.: 444,291

[30] Foreign Application Priority Data

| Feb. 23, 1973 | Germany | 2308941 |
|---|---|---|
| Jan. 18, 1974 | Germany | 2402354 |
| Jan. 18, 1974 | Germany | 2402352 |
| Jan. 23, 1974 | Germany | 2403120 |

[52] U.S. Cl. ......................... 260/561 K; 260/561 R
[51] Int. Cl.$^2$ .............. C07C 103/02; C07C 103/14
[58] Field of Search ..................... 260/561 R, 561 K

[56] References Cited
UNITED STATES PATENTS

| 3,037,055 | 5/1962 | Fierce et al. | 260/561 K |
| 3,494,734 | 2/1970 | Nakamura | 260/561 R |
| 3,615,192 | 10/1971 | Olivier | 23/151 |

*Primary Examiner*—C. Davis
*Attorney, Agent, or Firm*—Curtis, Morris & Safford

[57] ABSTRACT

By contacting hydrogen cyanide with oxygen or air and a catalyst solution containing water, low molecular weight aliphatic carboxylic acids, copper ions and nitrate ions oxalic acid diamide is formed in high yields.

29 Claims, No Drawings

PROCESS FOR THE PREPARATION OF OXAMIDE

The present invention relates to a process for the preparation of oxamide.

Oxalic acid diamide (oxamide) may be prepared according to different methods. Thus, for example, the heating of ammonium oxalate, the reaction of oxalic acid ester with ammonia and, in numerous publications, the partial hydrolysis of dicyan to form oxamide are described. The first two processes cited cannot be carried out because of economic reasons, while the third one seems to have been introduced into industrial practice. However, the use of dicyan had no satisfactory results until now since dicyan as such must be prepared from hydrocyanic acid and thus two process steps are necessary for the preparation of oxamide which, of course, causes a rise in price of the product.

For example, according to the process of German Auslegeschrift No. 1,297,589, hydrocyanic acid is reacted with $NO_2$ in aqueous solutions of copper(II) salts (for example copper nitrate) according to the following equation

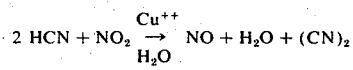

According to another process, dicyan may then be hydrolyzed in an aqueous mineral acid (without copper salts) to form oxamide, for example in accordance with the following equation:

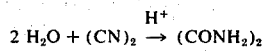

This latter process, known for a long time already (Chem. Ber. 1 (1868), 66), is also applied in the method described in German Patent No. 2,036,208. The combination of both these processes, however, has several disadvantages: it is for example necessary to provide a separate gas circuit in order to reoxidize NO to $NO_2$, further to use separate reactors for each of the process steps, and to remove by evaporation the water which is formed in the first step in order to prevent a dilution. Moreover, the required separation of $NO/(CN)_2$ and the heavy corrosive effect of the mineral acid cause serious problems.

It would be therefore appreciated if oxamide could be directly prepared from hydrocyanic acid in a single-step process without the formation of dicyan as intermediate product which must be isolated. In principle such a reaction has already been described by Attfield, Soc. 16 (1863), 95, but it is possible only by means of a several day reaction of hydrogen peroxide with aqueous hydrocyanic acid. This very slow reaction, however, apparently cannot be used in industrial practice.

A process has now been found for the preparation of oxamide which comprises contacting hydrogen cyanide (hydrocyanic acid) with oxygen or air and a catalyst solution containing water, lower aliphatic carboxylic acids, copper ions and nitrate ions.

The process of the invention is surprising in that, when hydrocyanic acid reacts with aqueous copper (II) salt solution, only dicyan is formed, a reaction known from the literature as the usual method for the preparation of dicyan. Nakamura (Ind. Eng. Chem. 7 (1968), 159 – 164) obtained some oxamide when he abandoned a copper nitrate solution containing hydrocyanic acid in low concentration for 3 days, but when he tried to accelerate the reaction by heating the solution to 100°C, substantially $CO_2$ was formed, while oxamide was obtained only with a maximum yield of 21 %. For this reason therefore, it was not to be expected that a simple addition of a lower aliphatic carboxylic acid allowed a catalytic reaction giving very good yields.

Since the reaction proceeds according to the following equation

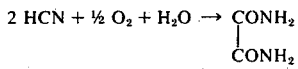

the presence of water in the catalyst solution is necessary. It has been found out that the water content of the catalyst solution should be from 3 to 80 %, preferably from 10 to 50 %. Generally, this amount of water is added from the start to the catalyst solution, and necessary after-dosage is carried out during the reaction. But it is also possible to feed in the water with water-containing hydrocyanic acid or by means of a wet current of air or oxygen.

The catalyst solution should contain from 19 to 96 %, preferably from 50 to 90 %, of lower aliphatic carboxylic acids. Suitable low molecular weight aliphatic carboxylic acids are formic, acetic, propionic, butyric, isobutyric acid or the straight chain and branched pentane-carboxylic acids. The acids should be completely dissolved in the catalyst solution. Acetic or formic acid are preferred. Mixtures of such carboxylic acids may also be used.

The content of copper nitrate, $Cu(NO_3)_2$, in the catalyst solution may widely vary; its upper limit is set by the solubility in the water containing acid; a copper nitrate concentration below 0.2 %, on the other hand, causes too slow a reaction. A concentration range of copper nitrate in the catalyst solution of from 1 to 10 % is preferred.

The reaction is carried out by feeding or pumping gaseous or liquid hydrocyanic acid into the catalyst solution. When aqueous or water-containing hydrocyanic acid is used, care has to be taken that the water content of the catalyst solution does not exceed the upper limit. As further reactant, air or oxygen is introduced into the catalyst solution, which reactant may be fed in separately, premixed or simultaneously with the hydrocyanic acid.

The ratio of oxygen to hydrocyanic acid should approximately correspond to the above equation, but an excess of oxygen does not adversely affect the course of the reaction. On the contrary, an excess of oxygen or air is even favorable, because, as compared to the addition of stoichiometric amounts of oxygen, the reaction is considerably accelerated. Thus, it is possible to react more hydrogen cyanide with the same amount of catalyst solution per unit of time and thus to increase the space-time yield of oxamide, calculated in grams per liter of reaction zone and hour. Furthermore, it has been observed that the risks of precipitation of copper-(I)-cyanide from the catalyst solution is clearly reduced by the excess of oxygen. It is also possible to feed in oxygen while stopping or reducing the introduction of hydrocyanic acid in order to prevent precipitation.

The upper limit of the amount of oxygen used in excess is set only by a reduction of the profitability of the process. The oxygen amount used should therefore not exceed sixfold the theoretical quantity. Since according to the above equation 0.25 mol of oxygen is employed per mol of hydrogen cyanide, the preferred oxygen amount should be from 0.25 to 1.5 mols per mol of hydrogen cyanide. Especially advantageous is above all an oxygen amount of two- to six-fold, preferably 2.5- to 4.5-fold, of the theoretical quantity.

Instead of excess oxygen, excess air or other oxygen containing gas mixtures may be employed in the same manner.

The water required for the reaction is introduced into the catalyst solution either directly or by means of the gas currents.

The reaction temperature in the catalyst solution should be in a range of from 0° to 120°C. Preferred operation temperatures are from 40° to 90°C. Since the reaction is exothermic, the desired temperature may be adjusted either by thermostating or by correspondingly setting the feed-in speed of the reactants.

The reaction pressure ranges from 0 to 50 atm/g. Operation at atmospheric pressure or slight overpressure up to 5 atm/g is preferred. Subatmospheric pressures or pressures above 50 atm/g are possible but not advantageous.

The reaction may be carried out batchwise or continuously, a continuous operation being preferred.

It has been observed in this latter operation that the reaction slows down after long duration; that is, less hydrogen cyanide is converted.

It has now been found that his disadvantage can be avoided by adjusting the pH of the catalyst solution to a value below 2.0 by addition of nitric acid. Preferably, a pH of from −1.0 to +1.5, especially from 0 to 1, is adjusted and maintained. By maintaining this optimum pH of the catalyst solution a long-term decrease of the space-time yield, calculated as grams of oxamide formed per liter of catalyst solution, is avoided.

The pH of the solution is measured at the optimum temperature of the catalyst of from 40° to 90°C, for example by means of a single-rod glass electrode of usual construction.

The nitric acid used for adjusting the desired pH may be added in any concentration degree whatsoever. Especially simple is the addition of commercial concentrated nitric acid to the recycled catalyst solution which is obtained as filtrate or centrifugate after the separation of the oxamide. Of course, a continuous introduction of nitric acid directly into the reactor is also possible.

Instead of nitric acid per se, also such substances may be used which form nitric acid under the reaction conditions, for example, acetyl nitrate. An addition of such substances is especially advantageous in the case where an oxygen excess is used or air is employed as oxidation agent.

When operating with the use of the catalyst solution in accordance with the present invention, there arise sometimes difficulties because of a too long induction time and an irregular course of the reaction.

It has now been found that these disadvantages can be avoided by adding soluble salts of low molecular weight aliphatic carboxylic acids and/or of nitric acid to the catalyst solution.

Without this addition, there is generally a certain induction time of from about 10 to 20 minutes before the reaction starts suddenly with heat decoloration of the solution. The longer the induction time, the faster generally the subsequent $O_2$ absorption and the higher the space-time yield within this period. This effect is especially obtained by adding iron-III-nitrate, which prolongs the induction time.

On the other hand, the induction time may be shortened to take only 2 to 3 minutes by adding other salts, for example $KNO_3$, $NaNO_3$, $Ca(NO_3)_2$ or potassium acetate. In such cases, the subsequent reaction is less violent and the absorption of $O_2$ proceeds more slowly. Also nickel salts reduce the induction time.

Furthermore, these additions have also an influence on the Cu content of the separated oxamide. In case of a rapid reaction and high space-time yield, the Cu content may amount to double to triple the Cu value obtained in a slow reaction.

Thus, by addition of the corresponding salts, which optionally may also be added one after the other in intervals, the induction time, the reaction speed and the copper content of the oxamide can be deliberately influenced. The lower the amount of copper being discharged with the oxamide, the longer the period within which the catalyst solution can be used.

As nitrates and/or salts of low molecular weight aliphatic carboxylic acids, practically salts of all those cations may be used which are soluble in the reaction medium. Preferred is the addition of ammonium, alkali metal and alkaline earth metal salts or salts of the groups III A and VIII of the Periodic System, especially salts of Li, Na, K, Mg, Ca, Al, Th, Ni or Fe. Besides the nitrates, suitable anions ae the acetates, formates, propionates or butyrates. It is recommended to use the salts of those carboxylic acids which are also present in the catalyst solution.

In any case, the presence of copper and nitrate ions in the catalyst solution is required. The amount of nitrates and/or salts of low molecular weight aliphatic carboxylic acids should be from the 0.1- to 10-fold molar amount of the copper nitrate.

In order to ensure a specific control of the reaction with respect to induction time, reaction speed and copper content of the oxamide, it is also possible to use mixtures of the cited salts in which cations as well as anions may be different.

It has furthermore been found that it is advantageous to recycle the gas mixture leaving the catalyst solution after complete reaction, and to contact it again with the catalyst solution. This gas mixture consists substantially of unconverted oxygen, hydrogen cyanide and, optionally, nitrogen. This gas circulation has several advantages: It is not necessary to control the reaction of the hydrogen cyanide according to the following equation $$2 HCN + \tfrac{1}{2} O_2 + H_2O \rightarrow H_2NCOCONH_2$$

to be quantitative; the non-reacted hydrogen cyanide still being present in the gas mixture thus is also recycled to the reaction solution, so that there are no losses.

In the same manner, unconverted oxygen too, which optionally may be also added in excess to the catalyst solution, is not lost when operating with gas circulation. Since in the case of using air or oxygen/air mixtures, also considerable amounts of hydrogen cyanide may be expelled from the catalyst solution before they have reacted, the recycling of the reaction gas ensures a conversion without losses also in this case. The use of air instead of oxygen is possible, but considerable amounts of waste gas must then be taken off in order not to elevate too much the inert gas level in the gas circuit. On the other hand, a preferred embodiment of this process provides starting the gas circuit with air or nitrogen. After feeding in the hydrogen cyanide, oxygen is added to the more or less nitrogen containing circulating gas in accordance with the consumption, that is, in an amount approximately corresponding to the above equation.

Because of the relatively elevated reaction temperature, it is difficult to ensure cooling only from the outside, especially when large-diameter reactors are used. Besides the cited components, the circulated gas contains also water and aliphatic carboxylic acids, for example acetic acid, the amount of which depends on the content of the catalyst solution and the temperature. By loading the large inert gas amount in the circulated gas with steam, it is very simple to educt the reaction heat from the catalyst liquid via a reflux condenser placed on top of the reactor or by a cooler in the gas circuit.

In most cases, the gase circuit is not completely closed but offers a possibility of taking off waste gas, which may be either fed in deliberately in the form of inert gas as described above, or carried along by slightly impure oxygen, or formed by side-reactions of the catalyst (small amounts of $CO_2$).

For carrying out the reaction, a flask-like or vessel-like recipient, but preferably a cylindrical vessel, is suitable, which vessel contains the catalyst solution. The oblong shape ensures a longer residence time. The gas mixture taken off at the top is pumped into the reactor again at the bottom, for example by means of a blowing device. The fresh oxygen may be added at a place before or after the blower or fed into the reactor via a special duct.

It may be advantageous to take off continuously portions of the catalyst solution and to recycle them into the reaction vessel. In the case where an oblong reactor in a vertical position is used, the catalyst solution is generally taken off at the top and fed in again at the bottom. By means of a corresponding compulsory circulation, it is also possible to lead the flow of the liquid in the opposite direction. The same goes for a reactor in horizontal or oblique position.

A circulation of catalyst has the following advantages: The risk of the crystallized solid oxamide formed in the reaction sticking to the reactor walls is reduced. When the speed of flow is high, the walls of the reactor remain free from oxamide layers, and thus a good passage of the reactants and a good heat dissipation through the walls are ensured. Furthermore, the circulation ensures an eduction of the considerable reaction heat by providing with a cooling device that part of the circulating apparatus where gas is absent, that is, generally, a descending branch of the catalyst cycle. Furthermore, a high speed of flow in the reactor charged with liquid has a favorable effect on the fine distribution of the reactants fed in gaseous form, that is, oxygen or oxygen/nitrogen mixtures and hydrogen cyanide. A finer distribution of the gases may be obtained by inserting a gas feeder valve in the circuit of the liquid.

When oblong reactors are used, the effect of preventing adhesion of oxamide ensured by the catalyst circulation is plainly demonstrated. By "oblong" reactors, there are to be understood those reactors the length of which is greater than the diameter, especially those where the ratio of length to diameter is from about 3 : 1 to 20 : 1, but other ratios may also be chosen.

The catalyst circulation may be the sole circuit in the process. However, it may be advantageous, for example in order to achieve a better cooling of the reaction medium, to circulate the catalyst solution as well as the gas, especially in a parallel current; the use of a flow tube for the reaction is also possible in this case. The catalyst may be circulated for example in a compulsory manner by means of a pump, or according to the mammoth pump principle where the liquid is conveyed in an upward direction by the gas amount blown in and then flows through a descending tube and enters the reactor again at the bottom. Also the thermosyphon principle may be employed for the catalyst circulation.

When the catalyst solution is circulated, an excess of oxygen may be used in order to achieve a better utilization of HCN and higher space-time yields. Advantageously, 2- to 6-fold of the theoretically required oxygen amount should be used.

The oxamide formed is practically insoluble in the catalyst solution and precipitates in crystallized form. It is removed from the reaction vessel continuously or batchwise and then separated from the adhering catalyst solution, for example by centrifugation or suction-filtration.

Under optimum conditions, the oxamide yields are higher than 95 %, relative to the hydrocyanic acid employed.

Oxamide may for example be used as organic intermediate product or directly as long-term fertilizer.

The following examples illustrate the invention.

EXAMPLE 1

A solution of 15 g of $Cu(NO_3)_2 . 3 H_2O$ in 320 g of glacial acetic acid and 80 g of water is introduced into a flask with agitator having a capacity of 1 liter and provided with a condenser mounted on its top. Within 4 hours, a total of 80 g of anhydrous hydrocyanic acid is allowed to flow into this solution with agitation and in a uniform current. Simultaneously, 5 liters of oxygen per hour are introduced. shortly after the feeding-in is started, the temperature rises to 70°C, and it is maintained at 50°– 60°C during the reaction period. After 4 hours, the test is stopped and the oxamide suspension which has formed is suction-filtered. The oxamide is washed with some dilute hydrochloric acid and subsequently with water, and dried. 123 g of pure oxamide are obtained, corresponding to 94.5 % relative to the hydrocyanic acid used.

COMPARATIVE EXAMPLE

Then operating in the same apparatus and under the same conditions as indicated above in Example 1 with the exception of adding glacial acetic acid, that is, using a solution of 15 g of $Cu(NO_3)_2 . 3 H_2O$ in 400 g of water, no oxamide is formed, even when the agitation is continued for 24 hours at 60° – 70°C.

EXAMPLE 2

When operating in the same apparatus as indicated in Example 1, and under the same conditions, but when 25 l of air per hour are introduced instead of oxygen, 121 g of oxamide are obtained, which corresponds to a yield of 92.7 % of the theoretical yield.

EXAMPLES 3 to 8

When operating in the same apparatus as indicated in Example 1, and under the same conditions, only with different concentrations of acetic acid, the following results are obtained:

Ex. 3: 40 % acetic acid gives 35 g oxamide = 26.8 % yield
Ex. 4: 50 % acetic acid gives 107 g oxamide = 82.0 % yield
Ex. 5: 60 % acetic acid gives 117 g oxamide = 89.7 % yield
Ex. 6: 70 % acetic acid gives 122 g oxamide = 93.5 % yield
Ex. 1: 80 % acetic acid gives 123 g oxamide = 94.5 % yield
Ex. 7: 90 % acetic acid gives 103 g oxamide = 79.0 % yield
Ex. 8: 95 % acetic acid gives 76 g oxamide = 58.3 % yield

EXAMPLE 9

In an apparatus as described in Example 1, a catalyst solution of 15 g of $Cu(NO_3)_2 \cdot 3H_2O$ in 320 g of formic acid and 80 g of water is introduced. Within 1 hour, 20 g of hydrocyanic acid and about 5 l of oxygen are allowed to flow into this solution. The temperature rises to 80° – 90°C and has to be maintained by cooling. When the precipitated oxamide is suction-filtered after 1 hour, 31 g of pure oxamide are obtained after washing and drying, corresponding to a yield of 95 % relative to the hydrocyanic acid used.

EXAMPLE 10

A catalyst solution of 15 g of $Cu(NO_3)_2 \cdot 3 H_2O$ in 320 g of propionic acid and 80 g of water is introduced into an apparatus as described in Example 1. Within 1 hour, 20 g of hydrocyanic acid and about 5 l of oxygen are allowed to flow in. The temperature rises to about 50°C, and, after the addition of the reaction gases is complete, it is maintained at 60° – 70°C for another 2 hours. According to the method described above, 29 g of oxamide corresponding to 89 % of the theoretical yield are isolated.

EXAMPLE 11

In the same manner as described in Example 10, with the only difference that n-butyric acid is used instead of propionic acid, 25 g of oxamide are obtained which corresponds to a yield of 76.6 %.

EXAMPLE 12

A solution of 5 g of $Cu(NO_3)_2 \cdot 3H_2O$ in 320 g of glacial acetic acid and 80 g of water is introduced into an apparatus as described in Example 1. Within 2 hours, 30 g of hydrocyanic acid and about 4 l of oxygen are allowed to flow into this solution. At an operation temperature of 75° – 80°C, 45 g of oxamide are obtained corresponding to a yield of 92 % relative to the hydrocyanic acid used.

EXAMPLE 13 (Comparative Example)

10 l of a catalyst solution containing 1.25% of $Cu(NO_3)_2 \cdot 3H_2O$ in 80% aqueous acetic acid are introduced into a glass tube in a vertical position having a diameter of 10 cm and a length of 1.50 m. At a temperature of 60°C, 500 g per hour of anhydrous hydrocyanic acid are pumped in, and simultaneously 110 – 115 l/h of oxygen are blown in, which correspond approximately to the stoichiometric amount. After about 20 minutes, the oxamide begins to precipitate. After 1 ½ hours, the catalyst solution having originally a blue color is nearly colorless, since a great part of the copper has precipitated in the form of CuCN. The catalyst solution no longer produces oxamide.

EXAMPLE 14

Under the same conditions as before, instead of 110 – 115 l of oxygen per hour, 250 l of oxygen per hour are introduced into the same apparatus as indicated in Example 13, which apparatus contains the same catalyst. Even after a four hour operation, the formation of oxamide is still going on in the same amounts, that is, an average of 740 g of oxamide per hour.

EXAMPLE 15

Instead of 110 – 115 l of oxygen per hour, 2.0 m³ of air are introduced into the same apparatus containing the same catalyst as indicated in Example 13, and under the same conditions. Even after a four hour operation, the formation of oxamide does not show any decrease. The yield is about 700 g of oxamide per hour.

EXAMPLE 16

The apparatus consists of a reaction tube having a diameter of 10 cm and a length of 1.50 m and a reflux condenser placed on top of the tube. 10 l of a catalyst solution containing 1.25 % of $Cu(NO_3)_2 \cdot 3H_2O$ in 80 % aqueous acetic acid are introduced into the reaction tube. The pH of the solution is 0.5. The apparatus is provided with a compulsory circuit which takes off the catalyst solution at the top of the reactor and feeds it in again at the bottom of the reactor with the aid of a centrifugal pump made of glass. The pump is adjusted in such a way that about 1000 l of liquid are circulated per hour. At a temperature of 60°C, 500 g of anhydrous hydrogen cyanide per hour are dosed in and about 350 l of oxygen per hour are blown in. The original pH of 0.5 rises to 1.2 within 2 hours. Subsequently, from 10 to 50 g of concentrated $HNO_3$ are added to the catalyst solution in intervals of 1 to 2 hours, thus maintaining the pH in a range of from 0 to 1.0. Even after 24 hours, the formation of oxamide with a yield of more than 95 % goes on without a decrease of the space-time yield.

EXAMPLE 17

When instead of oxygen about 2 m³ of air per hour are blown into the same apparatus under the same conditions as in Example 16, practically the same results are obtained. Only the addition of concentrated nitric acid has to be increased to 100 – 120 g per hour in order to maintain the desired pH in a range of from 0 to 1.0.

EXAMPLE 18

General test conditions:

The vessel has a capacity of 100 ml, it is double-walled and thermostated; gas feeder and exhaust tubes, dropping funnel, thermometer and glass electrode passing through the cover of the vessel, and the gas feeder tube being connected with an $O_2$ gas buret. A solution containing 0.97 g of $Cu(NO_3)_2 \cdot 3H_2O$ dissolved in a mixture of 32 ml of glacial acetic acid and 8 ml of $H_2O$ is introduced into the vessel, heated to 50°C and magnetically stirred. The whole system is flushed with $O_2$.

3 ml of hydrogen cyanide are contained in the dropping funnel, and this amount is added within 2 – 3 minutes starting from the beginning of the measuring operation. Since the $O_2$ absorption takes about 2 hours, the measuring error in measuring the induction time is relatively insignificant.

Result:

The induction time is 20 minutes, the $O_2$ absorption proceeds at a rate of 10 ml/minute, total absorption after 80 minutes: 380 ml, Cu content in the oxamide 0.080 % of Cu (after washing twice with water, further washing reduces the Cu content only insignificantly).

EXAMPLE 19

400 mg of $KNO_3$ are added to the reaction solution of Example 18, thus corresponding to a 0.1 m solution. Induction time 2 minutes, maximum $O_2$ absorption rate 10 ml/minute, total absorption 360 ml after 100 minutes, Cu content in the oxamide 0.042 % Cu.

EXAMPLE 20

1.0 g of Na-acetate are dissolved in the solution of Example 18. The induction time is 10 minutes, the average $O_2$ absorption rate is 4 ml/minute, total absorption 420 ml of $O_2$ in 120 minutes, Cu content in the oxamide 0.022 % Cu.

EXAMPLE 21

1.37 g of $Fe(NO_3)_3 \cdot 9H_2O$ are dissolved in the solution of Example 18 thus corresponding to a 0.1 m Fe-(III) solution.
Result:
Induction time 40 minutes, $O_2$ absorption rate 40 ml/minute, total absorption 400 ml of $O_2$ in 70 minutes, Cu content 0.060% Cu. When, in this Example, $Fe(NO_3)_3 \cdot 9H_2O$ is replaced by iron (III)acetate, practically the same values as indicated in Example 18 are obtained.

EXAMPLE 22

The operation mode is the same as indicated in Examples 19 to 21. 0.97 g of $Cu(NO_3)_2 \cdot 3H_2O$ and 0.58 g of $Ni(NO_3)_2 \cdot 6H_2O$ are dissolved in 40 ml of the 80 % acetic acid solution, so that the solution is 0.1 molar with respect to $Cu^{2+}$ and 0.05 molar with respect to $Ni^{2+}$. The reaction starts after 3 minutes, the absorption rate is 4 – 5 ml of $O_2$ per minute, total absorption 290 ml of $O_2$ after 105 minutes.

EXAMPLE 23

In the manner as indicated in Examples 19 to 22, 0.97 g of $Cu(NO_3)_2 \cdot 3H_2O$ and 0.5 g of $Mg(NO_3)_2 \cdot 6H_2O$ are dissolved in 40 ml of 80 % acetic acid solution, which corresponds to an about 0.05 molar $Mg^{2+}$ solution.
Induction time 8 minutes, average $O_2$ absorption rate 15 ml/minute. Cu content in the oxamide 0.171 %.

EXAMPLE 24

0.5 g of $TlNO_3$ are dissolved in the standard mixture as indicated in Example 18, which solution thus corresponds to a 0.047 molar Tl solution.
Induction time 12 minutes, absorption rate of $O_2$ 10 ml/minute. Cu content in the oxamide 0.035 %.

EXAMPLE 25

The apparatus consists of a vertically positioned reaction tube having a diameter of 10 cm and length of 1.50 m and a reflux condenser placed on top of it. The upper part of the reflux condenser is connected to the suction face of a gas diaphragm pump, the pressure face of which is connected with a feeder tube at the bottom of the reactor. The reaction tube is charged with a solution of 125 g of $Cu(NO_3)_2 \cdot 3H_2O$ in 8 l of glacial acetic acid and 2 l of water. At a temperature of 60°–70°C, the apparatus if filled with oxygen and the diaphragm pump for the gas circulation is adjusted in such a manner that about 500 l of gas are blown per hour in the lower part of the reactor via the feeder tube. The gas flows through the reactor from the bottom to the top, and the gas cooled by the condenser is again directed to the suction face of the gas circulation pump.

After the gas circulation is adjusted, 500 g of anhydrous hydrocyanic acid per hour are pumped in, and simultaneously 110 – 120 l of fresh oxygen are pumped to the suction face of the gas circulation pump. After a short starting period, formation of oxamide begins, which precipitates in the form of a crystal pulp, which is removed from the reaction sump and filtered off. 780 g of oxamide per hour are obtained.

EXAMPLE 26

The operations are carried out using the same apparatus and maintaining the same conditions as indicated in Example 25. After the catalyst solution is introduced into the reactor, such an amount of nitrogen is fed in that the gas circulation pump produces an over-pressure of about 100 mm Hg (measured at the pressure face). Under these conditions, 3 $m^3$ of gas per hour are pumped through the reactor. With 500 g of anhydrous hydrocyanic acid pumped in per hour and simultaneous addition of about 115 l of oxygen to the suction face of the pump with slight overpressure, 780 – 790 g of oxamide per hour are obtained.

EXAMPLE 27 (Comparative Example)

10 l of a catalyst solution containing 1.25% of $Cu(NO_3)_2 \cdot 3H_2O$ in 80% of aqueous acetic acid are introduced into a vertically positioned glass tube having a diameter of 10 cm and a length of 1.50 m. At a temperature of 60°– 70°C, 500 g of anhydrous hydrocyanic acid per hour are pumped in and simultaneously about 300 l of oxygen are passed through the reactor. The oxamide formation results in an average of 740 g per hour. After several hours, however, considerable amounts of solid crystallized oxamide are sticking to the walls which cause the apparatus to be switched off and a mechanical removal of the oxamide to be necessary.

EXAMPLE 28 (catalyst circulation)

The apparatus described in Example 25 is provided with a compulsory circuit by laterally deriving a duct having a diameter of 25 mm from the top of the reactor below the liquid level and by introducing it again into the reactor at its bottom with a centrifugal pump made of glass inserted. After the same catalyst solution as indicated in the Comparative Example is introduced into the reactor, the pump is switched on and thus a liquid circulation is adjusted at a rate of 1000 l per hour. At a temperature of 60°– 70°C, 500 g of anhydrous hydrogen cyanide and about 350 l of oxygen are dosed in per hour. After a several hour operation without any trouble, 740 – 750 g of oxamide are obtained per hour.

EXAMPLE 29

When operating as indicated in Example 28, but using about 2 $m^3$ of air instead of 350 l of oxygen, 720 – 740 g of oxamide are obtained per hour.

EXAMPLE 30 (catalyst and gas circulation)

The apparatus of Example 28 is provided with a jacket cooler in the descending part of the liquid circuit. The gas leaving the reactor at the top of the liquid column passes through a reflux condenser and is forwarded via a gas circulation pump which ensures that the unreacted gas from the top of the oblong reactor is again fed in at the bottom of the reactor. The apparatus is charged with the catalyst solution as indicated in the Comparative Example, heated to 60°–70°C, and a liquid circulation of about 100 l per hour is adjusted by means of the centrifugal pump. Subsequently, oxygen is fed into the apparatus, and a gas circulation of 500 – 700 l per hour is adjusted by means of the gas circulation pump. 500 g of anhydrous hydrogen cyanide are pumped per hour into this apparatus, and simultaneously, 110 – 120 l of oxygen per hour are fed in at the suction face of the gas circulation pump. The liberated reaction heat may be dissipated partially via the cooler in the descending branch of the liquid circuit, that is, in the absence of gas, and partially via the reflux condenser in the gas circuit. An average of 800 g of oxamide per hour is obtained.

EXAMPLE 31

When operating as indicated in Example 30, but with air instead of oxygen, the same results are obtained.

What is claimed is:

1. A process for the preparation of oxalic acid diamide which comprises reacting hydrogen cyanide, oxygen and water in a catalyst solution containing copper ions, nitrate ions and a low molecular weight aliphatic carboxylic acid, said catalyst solution containing from about 3% to about 80% of water by weight, from about 19% to about 96% of carboxylic acid by weight and at least about 0.2% of copper nitrate by weight, and isolating oxalic acid diamide from said catalyst solution.

2. A process according to claim 1 wherein said catalyst solution contains from about 10% to about 50% of water by weight.

3. A process according to claim 1 wherein said catalyst solution contains from about 50% to about 90% of said carboxylic acid by weight.

4. A process according to claim 1 wherein said catalyst solution contains from about 1% to about 10% of copper nitrate by weight.

5. A process according to claim 1 wherein said carboxylic acid is formic acid or acetic acid.

6. A process according to claim 1 wherein the reaction takes place at between 0° and about 120°C.

7. A process according to claim 1 wherein the reaction takes place at between about 40° and about 90°C.

8. A process according to claim 1 wherein the reaction takes place at a pressure of between about 0 and about 50 atm/g.

9. A process according to claim 1 wherein the reaction takes place at a pressure of between about 0 and about 5 atm/g.

10. A process according to claim 1 wherein the reaction is conducted continuously.

11. A process according to claim 10 wherein water is added to said catalyst solution during the course of the reaction.

12. A process according to claim 1 wherein said oxygen is supplied as air.

13. A process according to claim 1 wherein the reaction takes place in an excess of oxygen.

14. A process according to claim 13 wherein the amount of oxygen is about 2-fold to about 6-fold of the theoretical amount.

15. A process according to claim 13 wherein the amount of oxygen is about 2.5-fold to about 4.5-fold of the theoretical amount.

16. A process according to claim 1 wherein the pH of said catalyst solution is maintained below about 2.0 with nitric acid.

17. A process according to claim 16 wherein the pH of said catalyst solution is maintained at from about −1.0 to about +1.5.

18. A process according to claim 17 wherein the pH of said catalyst solution is maintained at from about 0 to about 1.

19. A process according to claim 16 wherein nitric acid is added to said catalyst solution.

20. A process according to claim 16 wherein substances are added to said catalyst solution that form nitric acid therein.

21. A process according to claim 1 wherein soluble salts of nitric acid or soluble salts of said carboxylic acid are added to said catalyst solution.

22. A process according to claim 21 wherein said salts are of the first to third main groups of the Periodic System.

23. A process according to claim 21 wherein iron salts are added.

24. A process according to claim 21 wherein nickel salts are added.

25. A process according to claim 1 wherein gas leaving from said catalyst solution after reaction is recycled back thereto.

26. A process according to claim 1 wherein a portion of said catalyst solution is removed during the reaction and then recycled back thereto.

27. A process according to claim 26 wherein said reaction is conducted in an oblong vessel.

28. A process according to claim 26 wherein gas leaving from said catalyst solution after reaction is recycled back thereto.

29. A process according to claim 28 wherein said reaction is conducted in an oblong vessel and said catalyst solution and said gas are recycled in parallel current.

* * * * *